(12) United States Patent
Grinberg

(10) Patent No.: US 7,014,617 B2
(45) Date of Patent: Mar. 21, 2006

(54) PIVOTED TENSIOMETER FOR MEASURING TENSION IN AN INTERVERTEBRAL DISC SPACE

(75) Inventor: Alexander Grinberg, Newton, MA (US)

(73) Assignee: Depuy Acromed, Inc., Paynham, MA (US)

( * ) Notice: Subject to any disclaimer, the term of this patent is extended or adjusted under 35 U.S.C. 154(b) by 545 days.

(21) Appl. No.: 10/247,864

(22) Filed: Sep. 20, 2002

(65) Prior Publication Data

US 2004/0059261 A1     Mar. 25, 2004

(51) Int. Cl.
*A61B 5/103*        (2006.01)

(52) U.S. Cl. ............... 600/587; 600/594; 606/102; 606/105

(58) Field of Classification Search ............... 600/587, 600/594; 33/511, 512; 73/379.01, 379.02, 73/379.03, 1.79; 606/86, 105, 102
See application file for complete search history.

(56) References Cited

U.S. PATENT DOCUMENTS

| | | | |
|---|---|---|---|
| 4,066,082 A | 1/1978 | Arcan et al. | |
| 4,271,836 A | 6/1981 | Bacal | |
| 4,432,376 A * | 2/1984 | Huszar | 600/587 |
| 4,501,266 A | 2/1985 | McDaniel | |
| 4,899,761 A | 2/1990 | Brown et al. | |
| 4,997,432 A * | 3/1991 | Keller | 606/61 |
| 5,213,112 A | 5/1993 | Niwa et al. | |
| 5,540,696 A | 7/1996 | Booth, Jr. et al. | |
| 5,997,545 A * | 12/1999 | Doherty et al. | 606/102 |
| 6,017,342 A | 1/2000 | Rinner | |
| 6,261,296 B1 * | 7/2001 | Aebi et al. | 606/90 |
| 6,716,218 B1 * | 4/2004 | Holmes et al. | 606/105 |
| 2002/0072752 A1 * | 6/2002 | Zucherman et al. | 606/99 |

FOREIGN PATENT DOCUMENTS

| | | | |
|---|---|---|---|
| FR | 2 356 405 A | | 1/1978 |
| WO | 00 19911 A | | 4/2000 |
| WO | 02 069811 A | | 9/2002 |

OTHER PUBLICATIONS

Partial European Search Report EP 03255768 dated Dec. 23, 2003.

* cited by examiner

*Primary Examiner*—Charles Marmor
*Assistant Examiner*—Rene Towa

(57) ABSTRACT

The present invention relates to a novel pivoted tensiometer adapted for use in measuring tension in an intervertebral disc space.

21 Claims, 3 Drawing Sheets

PIVOTED TENSIOMETER FOR MEASURING TENSION IN AN INTERVERTEBRAL DISC SPACE

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of bearing weight through a damaged, unstable vertebral joint. One conventional method of managing these problems is to remove the problematic disc and replace it with a prosthetic implant (such as a fusion body, spacer or a motion disk) within the intervertebral disc space.

Generally, intervertebral implant technology relies upon tension provided by natural ligaments adjacent the disc space to keep the implant in place. Accordingly, prior to insertion of the implant, it is typically desirable to measure the degree of tension afforded by these natural ligaments. However, a prevalent manner of measuring intervertebral tension requires the surgeon to insert a distractor into the disc space and manually "feel" the tension so produced. The subjectivity of this method may reduce its reliability.

U.S. Pat. No. 5,213,112 ("Niwa") discloses a tension meter comprising a main body, a fixed arm extending from one end of the main body, and a movable arm disposed parallel to the fixed arm and mounted on the main body so as to be movable away therefrom. In particular, the movable arm has a pair of proximal beams extending normally therefrom that are slidably received in a corresponding pair of throughholes disposed in the main body.

In use, the distal end of each arm is inserted into the disc space, the device is actuated to move the arms apart, and the force required to move the arms apart is measured.

However, since the distal end of the movable arm is subjected to a significant resisting force (from the resisting ligaments), the beam portion of the movable arm may jam in its corresponding hole, thereby reducing the accuracy of the device.

U.S. Pat. No. 4,501,266 ("McDaniel"), U.S. Pat. No. 4,899,761 ("Brown") and U.S. Pat. No. 5,540,696 ("Booth") each disclose a spinal distraction device utilizing a technology similar to Niwa in that the proximal beam portion of their movable arms is disposed in a barrel, and so is subject to the above-discussed jamming.

U.S. Pat. No. 4,066,082 ("Arcan") discloses a device for measuring tension in a disc space, comprising a pivotable device having a load cell fixed to the proximal and distal portions of a single arm and straddling the pivot. As the proximal portion of the device is deflected by stress applied to the jaws, a compressive force is registered in the load cell.

However, since the load cell is disposed about the pivot, the actual change in distance recorded by the load cell is small. Since the reported load is based upon this small change in distance, a small inaccuracy in recorded distance may lead to an inaccurate report of load. Of note, according to Arcan, great accuracy is not required in this technique.

SUMMARY OF THE INVENTION

In an embodiment of the present invention, there is provided a device for measuring tension in an intervertebral disc space in which distraction of the disc space is accomplished by a pivoted distraction device, and the force required to achieve the distraction is measured by a change in distance between the proximal portions of the longitudinal members of the device.

This embodiment is advantageous over the Niwa-type devices in that the pivot does not jam.

This embodiment is advantageous over the Arcan device because the change in distance between the proximal portions of the longitudinal members is much generally greater than that occurring about the pivot, and so can be much more accurately measured. Accordingly, the report of the corresponding loads associated with this change in distance may be much more accurate.

Therefore, in accordance with the present invention, there is provided a tensiometer for measuring tension in an intervertebral disc space, comprising:

a) a first longitudinal member having a distal end portion adapted for engaging a first vertebral surface, an intermediate portion, and a proximal handle portion having an attachment point, b) a second longitudinal member having a distal end portion adapted for engaging a second vertebral surface, an intermediate portion, and a proximal handle portion having an attachment point, the first and second longitudinal members being pivotally attached at a first pivot junction between the proximal handle and intermediate portions of each longitudinal member, and a load cell attached to each of the attachment points and adapted to report a load corresponding to a change in distance between the attachment points.

Also in accordance with the present invention, there is provided a method of measuring tension in an intervertebral disc space, comprising:

a) providing the above tensiometer,
b) advancing the distal tips of the distractor into the disc space,
c) changing the distance between the proximal portions of the longitudinal members, and
measuring the force produced by the step of changing the distance.

DETAILED DESCRIPTION OF THE INVENTION

For the purposes of the present invention, the term "supporting structures" refers to the ligaments and portions of the annulus fibrosus surrounding the disc space that experience tension when an inplant is inserted into the disc space. The term "disc space" refers to the space between opposing intervertebral bodies when at least a portion of the nucleus pulposus has been removed.

Figure 1:
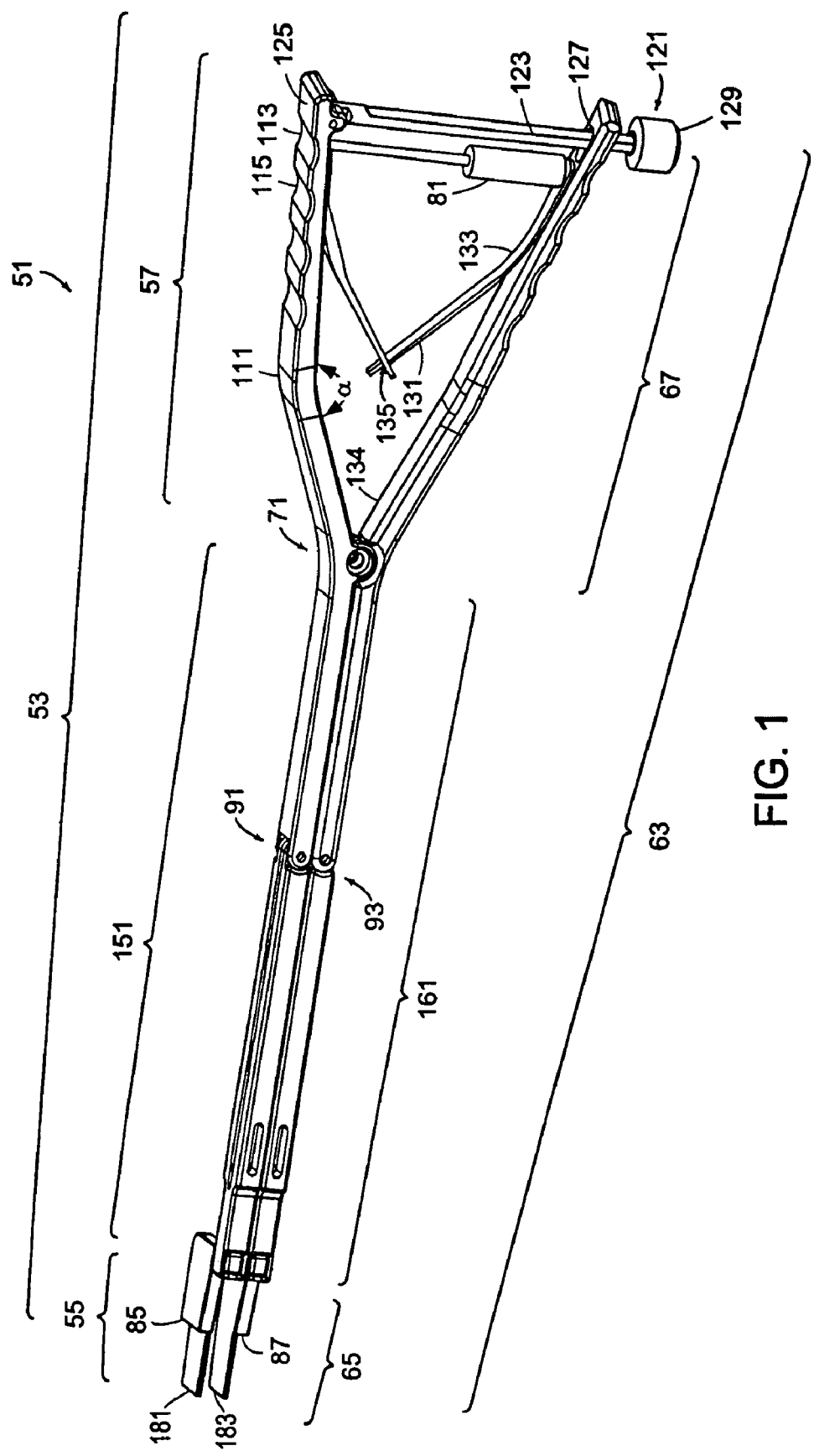
FIG. 1 discloses a perspective view of a preferred embodiment of the present invention in a closed position.
Figure 2:
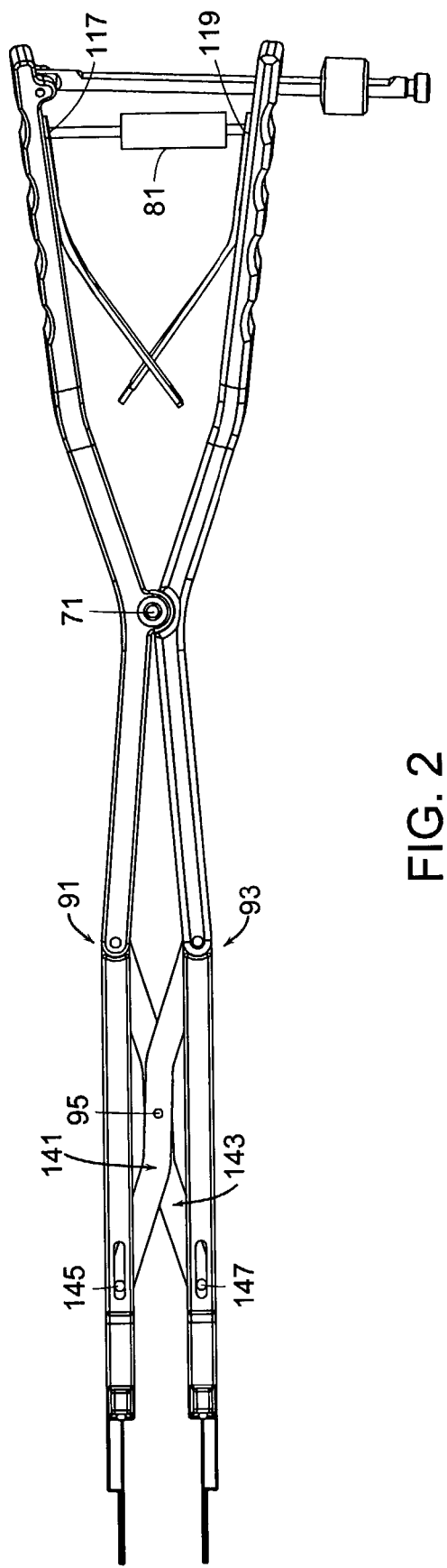
FIG. 2 discloses a perspective view of the FIG. 1 embodiment in an open position.
Figure 3:
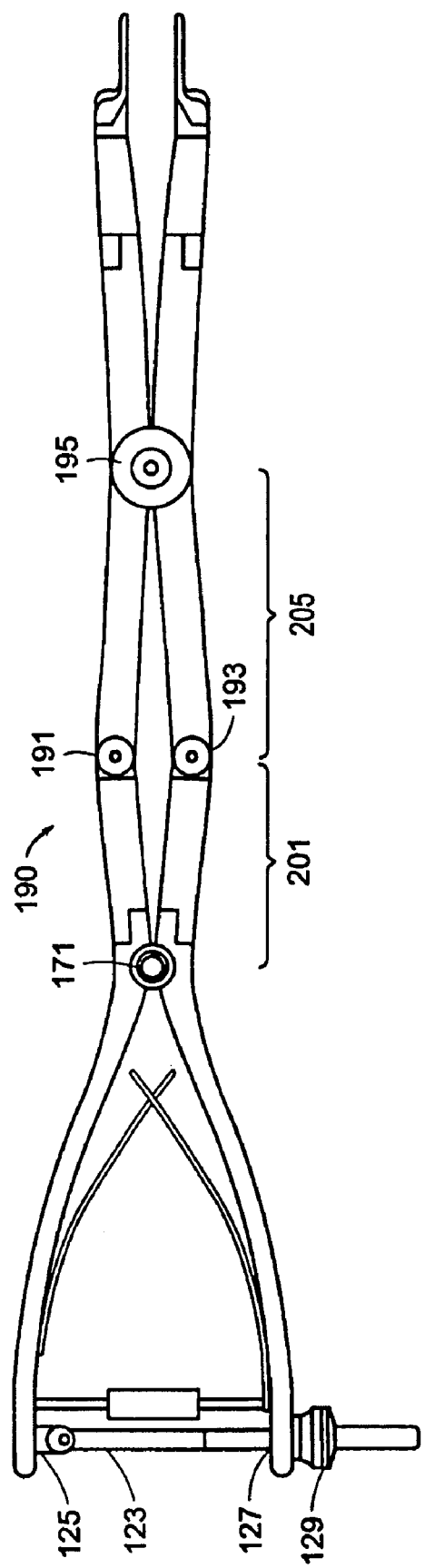
FIG. 3 discloses a perspective view of another preferred embodiment of the present invention in a closed position.

Now referring to FIGS. 1–3, there is provided a tensiometer 51 for measuring tension in an intervertebral disc space, comprising:

a) a first longitudinal member 53 having a distal end portion 55 adapted for engaging a first vertebral surface, an intermediate portion 151, and a proximal handle portion 57 having an attachment point 117, b) a second longitudinal member 63 having a distal end portion 65 adapted for engaging a second vertebral surface, an intermediate portion 161, and a proximal handle portion 67 having an attachment point 119, the first and second longitudinal members being pivotally attached at a pivot junction 71 between the proximal handle and intermediate portions of each longitudinal member, c) a load cell 81 attached to each of the attachment points and adapted to report a load corresponding to a change in distance between the attachment points of the proximal handle portions produced by the load.

The aim of the device of the present invention is to measure the tension within the disc space provided by the supporting structures and produced in response to the force imparted to the device needed to move apart its distal tips during distraction of the disc space. This is accomplished by measuring the force recorded by the proximally-disposed load cell in response to a change in the distance between the two attachment points located on the proximal handle portions of the longitudinal members.

Knowledge of the proper level of tension in a disc space allows a determination of the corresponding force required to provide complete distraction by a given distractor. The correspondence between the level of tension in a distracted disc space and the force required to distract the tips of a given distractor to produce that distraction can be determined through experimentation. Therefore, once the force required for a given distractor to distract its tips to a known height is obtained by the surgeon, the corresponding tension within the disc space can be easily calculated. Typically, the surgeon begins with small distraction heights producing requiring relatively low forces and correspondingly low tensions. The surgeon then proceeds to larger and larger distraction heights until the force registered for a given distractor is within the range of forces corresponding to the desired level of disc space tension. The distracted height corresponding to the most appropriate tension is then identified, and an implant of approximately that height is selected.

In some embodiments, the distal end portions of the tensiometer comprises distal tips 181,183. The distal tips of the distractor are adapted to enter the disc space and then distract the disc space by moving apart. Accordingly, the combined thickness of the distal tips should be less than that of the collapsed disc space, and preferably is as small as possible. The tips should be made of material strong enough to withstand the resisting forces of the supporting structures. The outer surfaces of the distal tips are preferably sufficiently smooth to avoid damaging the opposing vertebral walls.

In some embodiments, at least one of the distal end portions also comprises a proximally-positioned stop 85,87, which is designed to abut the front wall of at least one of the opposing vertebral bodies and prevent the surgeon from proceeding too far into the disc space.

Typically, the intermediate portions of each longitudinal member are adapted to transmit force from the proximal portion of the longitudinal member to the corresponding distal portions. Preferably, these intermediate portions have a long length (e.g., at least 10 times the length of the corresponding distal tip) sufficient to extend into the patient's body cavity, thereby allowing its use in anterior approach procedures.

In some embodiments, the intermediate portion of the longitudinal member consists essentially of a substantially rigid portion. This has the advantage of manufacturing simplicity.

In other embodiments, as in FIG. 3, the intermediate portion of each member form a double action pivot 190 comprising second 191 and third 193 pivots, and a fourth pivot 195 distal to the double action pivot, thereby defining proximal 201 and distal 205 portions of the intermediate portion. In the embodiment of FIG. 3, when the proximal handle portions are squeezed together, first pivot 171 causes a distal widening of the proximal portions of the intermediate portions, the double action pivot arrests the distal widening between the distal portions of the intermediate portions, and the fourth pivot causes a distal widening of the distal portions of the device. Because the double action pivot arrests the distal widening, it helps reduce the distance between the distal tips when the proximal handles are squeezed together. Since large distance changes between the proximal handles causes small distance changes between the tips, this device provides both mechanical advantage and sensitivity.

In the embodiment of FIG. 2, there is provided first and second cross bars 141,143 proximally pivotally attached to the longitudinal members at the proximal pivots 91,93; pivotally attached together at a fourth pivot 95; and slidably attached at their respective distal ends 145,147 to the opposing longitudinal member by a pin and groove arrangement. This parallel action embodiment has the advantage of producing parallel distal portions when the handles are squeezed together.

Therefore, in accordance with the present invention, there is provided a tensiometer for measuring tension in an intervertebral disc space, comprising:

a) a first longitudinal member having a distal end portion adapted for engaging a first vertebral surface, an intermediate portion, and a proximal handle portion having an attachment point, b) a second longitudinal member having a distal end portion adapted for engaging a second vertebral surface, an intermediate portion, and a proximal handle portion having an attachment point, the first and second longitudinal members being pivotally attached at a first pivot junction between the proximal handle and intermediate portions of each longitudinal member, c) a load cell connected to the tensiometer and adapted to report a load, wherein the intermediate portion of the first longitudinal member further comprises a second pivot located distal of the first pivot, the intermediate portion of the second longitudinal member further comprises a third pivot located distal of the first pivot, the second and third pivot forming a parallel action pivot.

The junction of the proximal handle and intermediate portions of each longitudinal member is adapted to accommodate a first pivot for pivotally attaching the longitudinal members. Preferably, the junction is located from the proximal handle end of the device a distance of between about 10–50% of the overall length of the device.

The first pivot is located at the junction between the intermediate and proximal handle portions of the longitudinal members and is adapted to effectively transmit force therebetween to open or close the more distal portions longitudinal members without causing deleterious jamming. In some embodiments, the first pivot is adapted so that, when the proximal handles are squeezed together, there is a narrowing of the longitudinal members. In other embodiments, the first pivot is adapted so that, when the proximal handles are squeezed together, there is a widening of the longitudinal members.

Typically, the proximal handle portions of each longitudinal member are adapted to produce a force to be transmitted distally when the proximal handle portions are moved either towards each other (in some instances) or away from each other (in some instances). Preferably, these proximal handle portions have a long length (e.g., at least 5 times the length of the corresponding distal tip) sufficient to extend into the patient's body cavity, thereby allowing its use in anterior approach procedures.

In some embodiments, the proximal handle portion consists essentially of a substantially straight beam portion. This has the advantage of simplicity in manufacturing.

In other embodiments, as in FIG. 1, the proximal handle portion comprises an angled intermediate portion 111. The angled portion has the advantage of reducing the distance between the proximal ends of the handle portions, and so is more user-friendly. The angled portion can also be designed to make the proximal ends of the handle portions more parallel. Typically, the angle $\alpha$ produced by this angled portion is between 120 and 150 degrees, and is typically disposed on the distal half of the proximal portion.

In preferred embodiments, the proximal portion of the handle portion has a surface 113 compatible for gripping by the surgeon. In some embodiments, these gripping surfaces are disposed on the outer facing surfaces 115 of the proximal portions of the handle portions.

Generally, the load cell reports the force required to produce a given response in a body having a known response to a load.

In some embodiments, the load cell comprises a compression spring. Preferably, this embodiment further comprises an indicator in connection with the compression spring, and preferably a graduated scale positioned to allow the surgeon to read the change in position of the indicator. This preferred type of load cell may operate on the same principle as a bathroom scale. Typically, the extent of compression of the spring in response to different loads has been predetermined. When a unidirectional force compresses the compression spring, the extent of displacement of the spring is measured and correlated to a force known to produce such displacement by the predetermined load-displacement relationship. The device then reports the force associated with the registered displacement.

In some embodiments, the load cell comprises an expansion spring. Preferably, this embodiment further comprises an indicator in connection with the expansion spring, and preferably a graduated scale positioned to allow the surgeon to read the change in position of the indicator. This preferred type of load cell may operate on the same principle as a grocer's hanging scale. Typically, the extent of expansion of the spring in response to different loads has been predetermined. When a unidirectional force expands the expansion spring, the extent of displacement of the spring is measured and correlated to a force known to produce such displacement by the predetermined load-displacement relationship. The device then reports the force associated with the registered displacement.

In some embodiments, the load cell is a Mechanical Force Gauge (Model X or U), available from Dillon Fairmount, Inc. of Fairmount, Minn. 56031. In some embodiments, the load cell is a stocked load cell, available from Sensotec, Inc. of Columbus, Ohio.

In the present invention, the load cell is disposed between handle portions of the longitudinal members and is positioned to respond to changes in the relative distance between a pair of attachment points fixed upon the handle portions of the longitudinal members. When the load cell is so disposed, it can respond to the relatively large distance changes experienced by these fixed attachment points. In contrast, the load cell of Arcan, positioned on each side of the pivot, responds to much smaller distance changes.

Preferably, the load cell is connected directly to the proximal portion of each handle portion at a pair of attachment points 117,119. Preferably, the load cell is pivotally attached to at least one attachment point, more preferably, to each attachment point. In general, the more proximal the attachment points, the greater the displacement thereof during use and the greater the opportunity to register an accurate load reading. Accordingly, the attachment points providing these attachments are preferably disposed on the proximal half of the handle portions of the longitudinal members, more preferably the proximal quarter of the handle portions of the longitudinal members.

In some embodiments of the present invention, a height indicator 121 is also disposed at least partially between handle portions of the longitudinal members. It typically comprises a graduated beam 123 pivotally attached to a proximal portion 125 of a first handle portion and positioned to slide through a through hole 127 positioned on a proximal portion of a second handle portion. Prior experimentation has determined the relationship between the displacement of the two connection points (of the height indicator) and the displacement between the two distal tips (which produce distraction). Thus, when the device is used and the distance between the connection points changes, the height indicator can report the corresponding distance between the distal tips by providing that corresponding distance on the graduated beam adjacent the through hole. Typically, the height indicator also has a stop 129 disposed at its unconnected end.

In some embodiments, resistance bars 131 are used. These bars each have a proximal end 133 attached to an interior surface 134 of the proximal handle and a distal end 135. The distal ends of the bars are connected to each other so as to produce a compression spring that resists movement of the proximal handle portions towards each other. Therefore, when the surgeon releases the handles the device reverts to its original position.

This prophetic example describes the operation and use of the spreader embodiment of the present invention.

First, the surgeon removes at least a portion of the intervertebral disc to create an intervertebral disc space.

Second, the surgeon orients the distal tips of the distractor so that the upper and lower walls thereof face the respective lower wall of the upper vertebral body and the upper wall of the lower vertebral body.

Third, the surgeon inserts the distal tips of the spreader into the disc space a predetermined distance such as 30 mm, stopping before the distal end of the spreader reaches the end of the disc space.

Fourth, the surgeon squeezes the handle portions towards each other, thereby forcing the distal tips apart and distracting the disc space.

Fifth, the surgeon reads the force displayed by the indicator provided on the load cell.

Sixth, the surgeon determines whether the desirable force has been reached.

If the surgeon determines that the displayed force is not within the desired range, then the surgeon selects a larger spreader and repeats steps 2–6 above.

If the surgeon determines that the displayed force is within the desired range, then the surgeon reads the display on the height indicator and selects an implant whose size corresponds to the distance displayed on the height indicator.

Eighth, the surgeon implants the selected implant.

Typically, the components of the present invention can be made out of any material commonly used in medical instruments. If the device is designed to be reusable, then it is preferred that all the components be made of stainless steel. If the device is designed to be disposable, then it is preferred that some of the components be made of plastic. Preferably, at least one component is sterilized. More preferably, each component is sterilized.

Preferably, the device of the present invention is used to measure the tension in an intervertebral disc space. In some embodiments, the disc space comprises opposing unprepared vertebral endplates. In some embodiments, the disc space comprises opposing vertebral endplates that have been prepared by a milling means. In some embodiments, the disc space includes at least a portion of an annulus fibrosus retained from the intervertebral disc. In other embodiments, both the nucleus pulposus and the annulus fibrosus have been removed. In some embodiments, the disk space has a height that is between 10% and 40% of the height of a healthy disc. In some embodiments, the disk space has a height that is between 40% and 60% of the height of a healthy disc. In some embodiments, the disk space has a height that is between 60% and 80% of the height of a healthy disc.

In preferred embodiments, as in FIG. 2, the proximal handle portion and the proximal portion of the intermediate section are made of a first single piece, while the distal portion of the intermediate portion and the distal portion of the device are made of a second single piece. In this embodiment, all of the portions of the first longitudinal member are disposed on the upper portion of the device.

In other embodiments, as in FIG. 3, the second single piece is shaped so as to cross over the fourth pivot, so that the first longitudinal member comprises the upper proximal handle, the upper intermediate portion, and the lower distal portion.

Typically, the thickness and spacing of the distal tips are predetermined to fit snugly within a typical collapsed disc space. In this condition, the first change in distance between the distracting tips produces a corresponding change in the height of the disc space. However, if the tips are undersized (i.e., the tips are relatively small so that their initial distraction does not distract the disc space, but only causes initial contact with the opposed endplates), the force required to make this initial contact should be substracted from the ultimate force measurement.

I claim:

1. A tensiometer for measuring tension in an intervertebral disc space, comprising:
 a) a first longitudinal member having a distal end portion adapted for engaging a first vertebral surface, an intermediate portion, and a proximal handle portion having an attachment point,
 b) a second longitudinal member having a distal end portion adapted for engaging a second vertebral surface, an intermediate portion, and a proximal handle portion having an attachment point, the first and second longitudinal members being pivotally attached at a first pivot junction between the proximal handle and intermediate portions of each longitudinal member, and
 c) a load cell attached to each of the attachment points and adapted to report a load corresponding to a change in distance between the attachment points,
wherein each distal end portion comprises a distal tip adapted to enter the disc space and distract the disc space when moved apart from each other, wherein the distal tips comprise two substantially parallel opposed plates adapted for distraction of the vertebral disc space.

2. The tensiometer of claim 1 wherein each intermediate portion and distal tip has a length, and the length of the intermediate portion is at least 10 times the length of the corresponding distal tip.

3. The tensiometer of claim 1 wherein at least one of the distal end portions comprises a proximally-positioned stop.

4. The tensiometer of claim 1 wherein each intermediate portion is substantially rigid.

5. The tensiometer of claim 1 wherein the first intermediate portion comprises a second pivot, the second intermediate portion comprises a third pivot, wherein the second and third pivots are positioned to form a double action pivot.

6. The tensiometer of claim 1 wherein the distal end portion further comprises first and second cross bars proximally pivotally attached to the respective first and second longitudinal members; pivotally attached together at a fourth pivot; and slidably distally attached to the respective second and first longitudinal members.

7. The tensiometer of claim 1 wherein the first pivot is located from a proximal handle end of the tensiometer a distance of between about 10–50% of an overall length of the tensiometer.

8. The tensiometer of claim 1 wherein the first pivot is adapted so that, when the proximal handle portions are squeezed together, the proximal portions of the intermediate portions move together.

9. The tensiometer of claim 1 wherein the first pivot is adapted so that, when the proximal handle portions are squeezed together, the proximal portions of the intermediate portions move apart.

10. The tensiometer of claim 1 wherein the proximal handle portions comprise an angled portion.

11. The tensiometer of claim 1 wherein the angled portion forms an angle of between 120 and 150 degrees.

12. The tensiometer of claim 1 wherein the load cell comprises a compression spring.

13. The tensiometer of claim 1 wherein the load cell comprises an expansion spring.

14. The tensiometer of claim 1 wherein the attachment points are disposed on the proximal half of the handle portions of the longitudinal members.

15. The tensiometer of claim 1 wherein the attachment points are disposed on the proximal quarter of the handle portions of the longitudinal members.

16. The tensiometer of claim 1 wherein further comprising a height indicator disposed at least partially between handle portions of the longitudinal members.

17. The tensiometer of claim 1 wherein further comprising first and second resistance bars, each bar having a proximal end attached to an interior surface of the proximal handle portion, and a distal end, the distal ends of the bars being connected to each other so as to produce a compression spring that resists movement of the proximal handle portions towards each other.

18. The tensiometer of claim 1 wherein the load cell is pivotally attached to at least one of the attachment points.

19. The tensiometer of claim 1 wherein the load cell is pivotally attached to each attachment point.

20. A method of measuring tension in an intervertebral disc space, comprising:
 a) providing a tensiometer comprising a distractor comprising:
  i) a first longitudinal member having a distal end portion adapted for engaging a first vertebral surface, an intermediate portion, and a proximal handle portion having an attachment point, ii) a second longitudinal member having a distal end portion adapted for engaging a second vertebral surface, an intermediate portion, and a proximal handle portion having an attachment point, the first and second longitudinal members being pivotally attached at a first pivot junction between the proximal handle and intermediate portions of each longitudinal member, and iii) a load cell attached to each of the attachment points and adapted to report a load corresponding to a change in distance between the attachment points, b) advancing the distal tips of the distractor into the disc space, c) changing the distance between the proximal portions of the longitudinal members, and d) measuring the force produced by the step of changing the distance.

21. A tensiometer for measuring tension in an intervertebral disc space, comprising:

a) a first longitudinal member having a distal end portion adapted for engaging a first vertebral surface, an intermediate portion, and a proximal handle portion having an attachment point, b) a second longitudinal member having a distal end portion adapted for engaging a second vertebral surface, an intermediate portion, and a proximal handle portion having an attachment point, the first and second longitudinal members being pivotally attached at a first pivot junction between the proximal handle and intermediate portions of each longitudinal member, and c) a load cell connected to the tensiometer and adapted to report a load, wherein the intermediate portion of the first longitudinal member further comprises a second pivot located distal of the first pivot, the intermediate portion of the second longitudinal member further comprises a third pivot located distal of the first pivot, the second and third pivot forming a parallel action pivot, wherein each distal end portion comprises a distal tip adapted to enter the disc space and distract the disc space when moved apart from each other, wherein the distal tips comprise two substantially parallel opposed plates adapted for distraction of the vertebral disc space.

* * * * *